(12) United States Patent
Worthen

(10) Patent No.: US 6,460,544 B1
(45) Date of Patent: Oct. 8, 2002

(54) METHOD AND APPARATUS FOR ESTABLISHING AND MAINTAINING THERAPEUTIC HYPOTHEMIA

(75) Inventor: William J. Worthen, Coto de Caza, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 09/498,499

(22) Filed: Feb. 4, 2000

Related U.S. Application Data

(63) Continuation-in-part of application No. 09/266,452, filed on Mar. 11, 1999.

(51) Int. Cl.$^7$ ............................................. A61B 19/00
(52) U.S. Cl. ........................ 128/898; 607/105; 607/106; 606/20; 606/27
(58) Field of Search ............................. 606/27, 28, 29, 606/30, 31, 32, 20; 607/96, 98, 105, 104, 106, 113; 128/898

(56) References Cited

U.S. PATENT DOCUMENTS

| | | |
|---|---|---|
| 2,058,780 A | 10/1936 | Elliot |
| 2,077,453 A | 4/1937 | Albright |
| 3,142,158 A | 7/1964 | Podolsky |
| 3,425,419 A | 2/1969 | Dato |
| 3,460,538 A | 8/1969 | Armstrong |
| 4,111,209 A | 9/1978 | Wolvek |
| 4,181,132 A | 1/1980 | Parks |
| 4,476,867 A | 10/1984 | Parks |
| 4,479,798 A | 10/1984 | Parks |
| 4,540,402 A | 9/1985 | Aigner |
| 4,747,826 A | 5/1988 | Sassano |
| 4,860,744 A * | 8/1989 | Johnson et al. ............... 62/3.2 |
| 4,919,134 A | 4/1990 | Streeter |
| 5,011,468 A | 4/1991 | Lundquist et al. |
| 5,059,167 A | 10/1991 | Lindquist et al. |
| 5,149,321 A | 9/1992 | Klatz et al. |
| 5,234,405 A | 8/1993 | Klatz et al. |

(List continued on next page.)

OTHER PUBLICATIONS

U.S. patent application Ser. No. 09/133,813, Noda et al., App. Pending.
U.S. patent application Ser. No. 09/266,452, Evans et al., App Pending.
U.S. patent application Ser. No. 09/282,971, Philips., App Pending.
U.S. patent application Ser. No. 09/390,600, Luo et al., App Pending.
U.S. patent application Ser. No. 09/413,752, Evans et al., App Pending.
U.S. patent application Ser. No. 09/413,753, Evans et al., App Pending.
U.S. patent application Ser. No. 09/427745, Pham et al., App Pending.

(List continued on next page.)

Primary Examiner—Rosiland Stacie
(74) Attorney, Agent, or Firm—John L. Rogitz

(57) ABSTRACT

A kit for establishing and maintaining hypothermia in a patient for neurotherapeutic purposes includes a high cooling capacity catheter that is advanced into the patient's central venous system to quickly cool the patient to, e.g., 32° C. or so. Once hypothermia has been established, the high capacity catheter is removed and replaced with a lower cooling capacity catheter which maintains a desired reduced temperature. The lower capacity catheter advantageously can be configured as a central venous catheter for permitting the catheter to be used for multiple functions. Alternatively, the high cooling capacity catheter can be used to attenuate a fever and lower the patient's body temperature to normal, with the lower capacity catheter being used to maintain normal body temperature.

5 Claims, 2 Drawing Sheets

U.S. PATENT DOCUMENTS

| | | | |
|---|---|---|---|
| 5,308,320 A | * | 5/1994 | Safar et al. ............ 604/4 |
| 5,395,314 A | | 3/1995 | Klatz et al. |
| 5,437,673 A | | 8/1995 | Baust |
| 5,486,208 A | | 1/1996 | Ginsburg |
| 5,531,776 A | | 7/1996 | Ward et al. |
| 5,624,392 A | | 4/1997 | Saab |
| 5,695,457 A | | 12/1997 | St. Goar et al. |
| 5,716,386 A | | 2/1998 | Ward et al. |
| 5,837,003 A | * | 11/1998 | Ginsburg ............ 607/106 |
| 5,871,526 A | | 2/1999 | Gibbs et al. |
| 5,879,316 A | | 3/1999 | Safar et al. |
| 5,906,588 A | | 5/1999 | Safar et al. |
| 6,019,783 A | | 2/2000 | Philips et al. |
| 6,126,684 A | | 10/2000 | Gobin et al. |
| 6,149,670 A | | 11/2000 | Worthen et al. |
| 6,190,356 B1 | | 2/2001 | Bersin |
| 6,231,594 B1 | | 5/2001 | Dae |
| 2001/0005791 A1 | * | 6/2001 | Ginsburg et al. |

OTHER PUBLICATIONS

U.S. patent application Ser. No. 09/456,110, Luo et al., App Pending.

U.S. patent application Ser. No. 09/477,490, Lasersohn et al., App Pending.

U.S. patent application Ser. No. 09/503,014, Gobin et al., App Pending.

U.S. patent application Ser. No. 09/494,896, Philips et al., App Pending.

U.S. patent application Ser. No. 09/498,499, Worthen., App Pending.

U.S. patent application Ser. No. 09/540,693, Worthen et al., App Pending.

U.S. patent application Ser. No. 09/546,814, Gobin et al., App Pending.

U.S. patent application Ser. No. 09/565,039, Worthen et al., App Pending.

Bernard, S., Induced Hypothermia in Intensive Care Medicine, *Anaesth. Intensive Care*, 1996 Jun., 24(3):382–388.

Gillinov Et Al., Superior Cerebral Protection With Profound Hypothermia During Circulatory Arrest, *Annals of Thoracic Surgery*, 1993 Jun., 55(6):1432–1439.

Ginsberg Et Al., Therapeutic Modulation of Brain Temperature: Relevance to Ischemic Brain Injury, *Cerebrovascular and Brain Metabolism Reviews*, 1992 Fall, 4(3):189–225.

Marion Et Al., Resuscitative hypothermia, *Critical Care Medicine*, 1996 Feb., 24(2):S81–S89.

Marion Et Al., Treatment of traumatic brain injury with moderate hypothermia, *The New England Journal of Medicine*, 1997 Feb., 336(8):540–546.

Sessler, D., Deliberate Mild Hypothermia, *Journal of Neurosurgical Anesthesiology*, 1995, Jan., 7(1):38–46.

\* cited by examiner

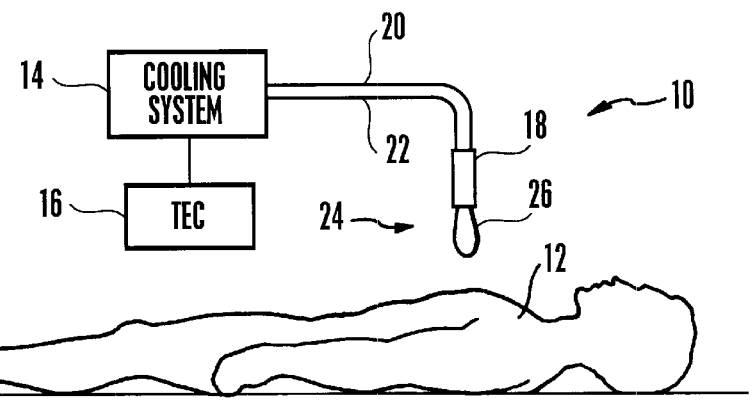
Figure 1 - high capacity catheter cool down
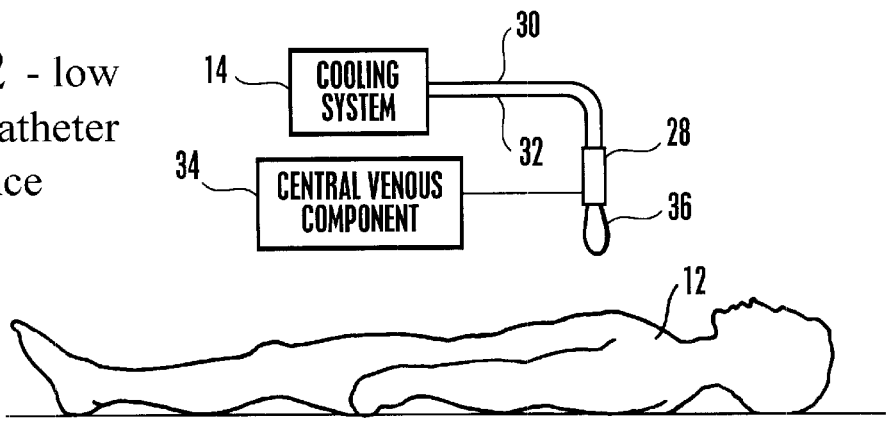
Figure 2 - low capacity catheter maintenance
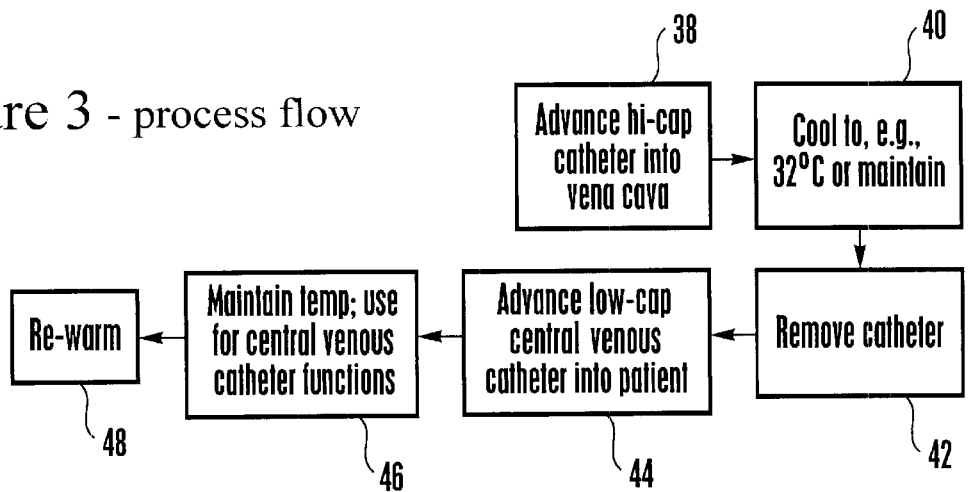
Figure 3 - process flow

US 6,460,544 B1

METHOD AND APPARATUS FOR ESTABLISHING AND MAINTAINING THERAPEUTIC HYPOTHEMIA

The present application is a C-I-P from co-pending U.S. patent application Ser. No. 09/266,452, filed Mar. 11, 1999.

FIELD OF THE INVENTION

The present invention relates generally to methods and apparatus for cooling patients for therapeutic purposes, and more particularly to systems for treating brain trauma and brain ischemia such as that caused by cardiac arrest by inducing hypothermia in a patient.

BACKGROUND

It has been discovered that the medical outcome for a patient suffering from severe brain trauma or from ischemia caused by stroke or heart attack is degraded if the patient's body temperature rises above normal (38° C.). It is further believed that the medical outcome for many such patients might be significantly improved if the patients were to be cooled relatively quickly for a short period, e.g., 12–72 hours.

Systems and methods have been disclosed that propose cooling blood flowing to the brain through the carotid artery. An example of such systems and methods is disclosed in co-pending U.S. patent application Ser. No. 09/063,984, filed Apr. 21, 1998, owned by the present assignee and incorporated herein by reference. In the referenced application, various catheters are disclosed which can be advanced into a patient's carotid artery and through which coolant can be pumped in a closed circuit, to remove heat from the blood in the carotid artery and thereby cool the brain. The referenced devices have the advantage over other methods of cooling (e.g., wrapping patients in cold blankets) of being controllable, relatively easy to use, and of being capable of rapidly cooling and maintaining blood temperature at a desired set point.

As recognized in co-pending U.S. patent application Ser. No. 09/133,813, filed Aug. 13, 1998, owned by the present assignee and incorporated herein by reference, the above-mentioned advantages in treating brain trauma/ischemic patients by cooling can also be realized by cooling the patient's entire body, i.e., by inducing systemic hypothermia. The advantage of systemic hypothermia is that, as recognized by the present assignee, to induce systemic hypothermia a cooling catheter or other cooling device need not be advanced into the blood supply of the brain, but rather can be easily and quickly placed into the relatively large vena cava of the central venous system. Moreover, since many patients already are intubated with central venous catheters for other clinically approved purposes anyway, providing a central venous catheter that can also cool the blood requires no additional surgical procedures for those patients. A cooling central venous catheter is disclosed in the present assignee's co-pending U.S. patent application Ser. No. 09/253,109, filed Feb. 19, 1999 and incorporated herein by reference.

The present invention recognizes that a patient requiring hypothermia preferably be cooled down relatively rapidly. Thus, catheters with high cooling capacities, such as the catheter that is the subject of the second of the above-referenced applications, are desirable. As recognized herein, however, it is not necessary to maintain a high capacity catheter in a patient once the patient has been cooled, provided a catheter with lower cooling capacity is used to maintain temperature at the desired level. The present invention understands that such a lower cooling capacity catheter, which can be configured as, e.g., a central venous catheter to facilitate uses other than just cooling, can be advantageously used to replace the higher capacity catheter to maintain temperature.

SUMMARY OF THE INVENTION

A kit for lowering and maintaining temperature in a patient includes a groin catheter having at least one fluid circulation passageway connectable to a source of coolant. The groin catheter is configured for placement in a patient's circulatory system through a groin entry point. A neck catheter has at least one fluid circulation passageway connectable to a source of coolant, with the neck catheter being configured for placement in a patient's circulatory system through a neck entry point.

In a preferred embodiment, the groin catheter has a first cooling capacity and the neck catheter has a second cooling capacity less than the first cooling capacity. Both catheters preferably have respective heat exchange regions that are established by one or more balloons.

In another aspect, a method for establishing and maintaining a predetermined temperature in a patient includes lowering the patient's temperature to a desired level using a groin catheter at least partially placed in the venous system of the patient, and maintaining the temperature at the desired level using a neck catheter having a heat exchange region.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a schematic view of the cooling system using the high cooling capacity catheter;

FIG. 2 is a schematic view of the cooling system using the low cooling capacity central venous catheter;

FIG. 3 is a flow chart of the present invention for establishing and maintaining hypothermia in a patient.

DETAILED DESCRIPTION OF THE PREFERRED EMBODIMENT

Figure 4:
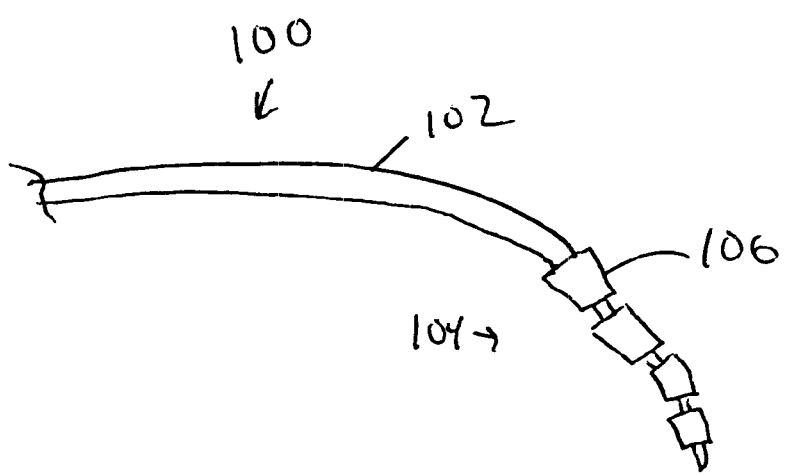
FIG. 4 is a schematic view of an alternate high capacity catheter.

Referring initially to FIG. 1, a therapeutic system, generally designated 10, is shown for establishing and maintaining hypothermia in a patient 12, or for attenuating a fever spike in a patient and then maintaining normal body temperature in the patient. As shown, the system 10 includes a cooling system 14 that can be a water-bath system such as the system disclosed in the present assignee's co-pending U.S. patent application Ser. No. 09/220,897 and incorporated herein by reference, or a cooling system including at least one thermal electric cooler (TEC) 16, as disclosed in the present assignee's co-pending U.S. patent application Ser. No. 09/260,950 and incorporated herein by reference. In any case, the cooling system 14 can be considered a source of coolant, preferably sterile saline, for the catheters of the present invention.

As set forth in these applications, the cooling system 14 can include a heat exchanger, a pump, and, if desired, a controller. Preferably, the pump is a peristaltic pump, but other types of positive displacement pumps, such as but not limited to piston pumps and gear pumps, or even centrifugal pumps, can be used. A peristaltic pump is preferred in the present implementation because it can pump coolant without directly contacting the coolant, but instead simply by squeezing a tube through which the coolant flows. In this way, the pump is reusable, and only the present catheters and portions of the system 10 coming in direct contact with the coolant need be made disposable to render an advantageously disposable and sterile coolant delivery system. The controller controls the rate at which coolant is pumped by the pump and, if desired, the rate at which heat is added or subtracted from the coolant. The controller can be implemented by a software-executing processor or by discrete logic circuits or other electronic circuitry device to establish a desired patient temperature by appropriately controlling the pump and/or heat exchanger in response to a temperature signal derived from a sensor in the patient 12.

As shown in FIG. 1, a high cooling capacity catheter 18 can communicate with the cooling system 14 via coolant supply and return lines 20, 22. The coolant lines 20, 22 can be IV lines or tubes or other suitable fluid conduits, such as metal (steel) tubes. When the coolant lines 20, 22 are plastic tubes, they can be connected to the catheter 18 and the cooling system 14 by suitable connecting structure, such as Luer fittings, interference fits, solvent bonding, heat staking, ultrasonic welding, and the like.

The high cooling capacity catheter 18 includes a heat exchange region 24 that in turn can include one or more hollow fibers 26, as disclosed in the above-referenced U.S. patent application Ser. No. 09/133,813. As set forth in the '813 application, coolant is circulated in a closed fluid communication loop between the hollow fibers 26 and cooling system 14 to remove heat from the patent 12. By "high cooling capacity" is meant the ability to cool down a 150 pound mammal from normal body temperature to about 6° C. below normal body temperature at a rate of at least one and one-half degrees per hour (1.5° C./hr.). As set forth in greater detail below, the high capacity catheter 18 is advanced (preferably through an introducer sheath) into the patient 12 through a groin entry point to establish hypothermia in the patient 12, or to attenuate a fever back to normal body temperature. Preferably, the catheter 18 is advanced into the central venous system, and more preferably into the vena cava, either through the saphenous vein or femoral vein.

Once hypothermia or non-elevated temperature has been established, the high capacity catheter 18 can be removed, if desired, from the patient, and temperature maintained at a desired normal or hypothermic level by using a lower (relative to the capacity of the high capacity catheter 18) cooling capacity catheter 28. In the preferred embodiment, the lower capacity catheter 28 is configured for use as a central venous catheter, and can be embodied by the catheter disclosed in the above-referenced patent application Ser. No. 09/253,109. Accordingly, the lower capacity catheter 28 can communicate with the cooling system 14 via coolant supply and return lines 30, 32. Also, the lower capacity catheter 28 can communicate with one or more central venous components 34, such as IV infusion devices, drug delivery syringes, blood withdrawal devices, and so on as are commonly used in connection with central venous catheters for undertaking respective central venous catheter functions.

As disclosed in the referenced application Ser. No. 09/253,109 the lower capacity catheter 28 includes a heat exchange region through which coolant from cooling system 14 is circulated in a closed loop. In the preferred embodiment, the heat exchange region is established by one or more balloons 36, although it could be established by hollow fibers in the manner of the catheter 18, but on a smaller scale. The catheter 28 can be advanced through a neck entry point into the superior vena cava through the jugular vein or subclavian vein to cool the patient 12 by means of coolant circulating in a closed loop between the cooling system 14 and the balloon 36. As mentioned above, the lower capacity catheter 28 can also be used to undertake conventional central venous catheter functions.

Alternatively, the high capacity catheter of the present invention can be established by a catheter 100, as shown in brief reference to FIG. 4, which is in all essential respects identical to the lower capacity catheter 28 with the exception that the catheter 100 has a relatively long body 102, to facilitate advancing a distal heat exchange region 104 through the groin into the vena cava. Also, the heat exchange region 104 of the catheter 100 can be established by larger balloons 106 or a greater number of balloons (four are shown in FIG. 4) as compared to the heat exchange region of the lower capacity balloon 28. As yet another alternative, the heat exchange capacities of the balloons 28, 100 can be about equal to each other.

The process of the present invention can be appreciated in reference to FIG. 3. Commencing at block 38, the heat exchange region of a groin catheter such as, e.g., the high capacity catheter 18 or 100 is advanced into the vena cava of the patient 12 through the saphenous vein or femoral vein. The patient 12 is relatively quickly and precisely cooled to, e.g., 32° C.–34° C. using the high capacity catheter 18 or 100 at block 40 when hypothermia is indicated as a treatment. Or, when it is desired merely to attenuate a fever spike, the patient can be relatively quickly and precisely cooled to 38° C. In any event, to effect a "soft landing" to the desired temperature, as the body temperature approaches the desired level warm coolant can be circulated through the catheter 18 in lieu of cold coolant.

Once the desired body temperature has been established, the high capacity catheter 18 or 100 can be removed, if desired, at block 42, and the lower capacity catheter 28 advanced into the vena cava at block 44 through the neck (jugular vein or subdlavian vein), it being understood that the step at block 42 can be omitted if desired and both catheters 18, 28 be present simultaneously in the patient. Moving to block 46, the desired patient temperature is maintained using the lower capacity catheter 28. Also, when the catheter 28 is configured as a central venous catheter, it can be used to undertake the central venous catheters mentioned above. At block 48, when hypothermia has been induced and treatment is completed, the patient is rewarmed to normal body temperature by circulating warm coolant through the catheter 28.

While the particular METHOD AND APPARATUS FOR ESTABLISHING AND MAINTAINING THERAPEUTIC HYPOTHERMIA as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for".

What is claimed is:

1. A method for establishing and maintaining a predetermined temperature in a patient, comprising the acts of:

lowering the patient's temperature to a desired level using a groin catheter at least partially placed in the venous system of the patient; and maintaining the temperature at the desired level using a second catheter having a heat exchange region placed in the patient's venous system, both catheters circulating coolant in a closed loop such that the coolant does not contact the blood.

2. The method of claim 1, wherein the first catheter includes at least one balloon.

3. The method of claim 1, wherein the heat exchange region of the second catheter includes at least one balloon.

4. The method of claim 1, comprising the act of removing the first catheter from the patient prior to the maintaining act.

5. The method of claim 1, comprising the act of undertaking one or more central venous line functions using the second catheter during the maintaining act.

* * * * *